US012806003B2

(12) United States Patent
Richardson et al.

(10) Patent No.: US 12,806,003 B2
(45) Date of Patent: Nov. 24, 2026

(54) INSERTION CARTRIDGES WITH REDUCED IOL STRESS

(71) Applicant: Johnson & Johnson Surgical Vision, Inc., Irvine, CA (US)

(72) Inventors: Gary Richardson, Jacksonville, FL (US); Leslie A. Voss, Jacksonville, FL (US); Edward R. Kernick, Jacksonville, FL (US); Yasemar Perez, Aguadilla, PR (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 784 days.

(21) Appl. No.: 18/151,300

(22) Filed: Jan. 6, 2023

(65) Prior Publication Data

US 2023/0225857 A1 Jul. 20, 2023

Related U.S. Application Data

(60) Provisional application No. 63/266,932, filed on Jan. 19, 2022.

(51) Int. Cl.
*A61F 2/16* (2006.01)

(52) U.S. Cl.
CPC .................................... *A61F 2/167* (2013.01)

(58) Field of Classification Search
CPC ............................... A61F 2/167; A61F 2/1678
See application file for complete search history.

(56) References Cited

U.S. PATENT DOCUMENTS

| | | | | |
|---|---|---|---|---|
| 5,702,400 | A | 12/1997 | Brown et al. | |
| 5,928,245 | A | 7/1999 | Wolf et al. | |
| 5,947,976 | A | 9/1999 | Van Noy et al. | |
| 6,010,510 | A | 1/2000 | Brown et al. | |
| 6,056,757 | A * | 5/2000 | Feingold | A61F 2/1664 606/107 |

(Continued)

FOREIGN PATENT DOCUMENTS

| | | | |
|---|---|---|---|
| DE | 102019128370 | B3 | 12/2020 |
| EP | 2324797 | B1 | 5/2019 |

(Continued)

*Primary Examiner* — Ashley L Fishback
*Assistant Examiner* — Chima U Igboko
(74) *Attorney, Agent, or Firm* — Troutman Pepper Locke LLP

(57) ABSTRACT

An intraocular lens (IOL) injector cartridge having one or more modifications from conventional designs which reduce stress and strain in the optic of the IOL during passage through the cartridge. One change includes adding axially-oriented ribs in a funnel portion of the cartridge to enable the cartridge wall to flex outward during passage of the IOL, which is compressed to a great degree in the cartridge lumen. Another modification involves providing a longitudinal step along a segment of the inner lumen which biases one free edge of the optic to tuck or dive under the other free edge and encourage spiral folding as the IOL progresses along the gradually narrowing lumen. The third option is modifying the shape of the lumen within the extreme distal end of the cartridge where the lumen is smallest so that it is neither circular nor oval. Each or all of these modifications may be incorporated into a single cartridge.

8 Claims, 13 Drawing Sheets

(56) References Cited

U.S. PATENT DOCUMENTS

| | | | | |
|---|---|---|---|---|
| 8,273,122 | B2 | 9/2012 | Anderson | |
| 8,894,664 | B2 | 11/2014 | Downer | |
| 2001/0007075 | A1 | 7/2001 | Hjertman et al. | |
| 2013/0165943 | A1* | 6/2013 | Downer ................ | A61F 2/1678 606/107 |
| 2015/0018836 | A1* | 1/2015 | Rathert ................... | A61F 2/167 606/107 |
| 2019/0105151 | A1* | 4/2019 | Tseng .................... | A61F 2/1691 |

FOREIGN PATENT DOCUMENTS

| | | | |
|---|---|---|---|
| WO | 9837830 | A2 | 9/1998 |
| WO | 0062712 | A1 | 10/2000 |
| WO | 2011132199 | A1 | 10/2011 |
| WO | 2022263200 | A1 | 12/2022 |

* cited by examiner 64
68

68
72
74
67
75

60
62
5
5
72
74
66

62
72
74
66

INSERTION CARTRIDGES WITH REDUCED IOL STRESS

RELATED APPLICATIONS

The present application claims priority to Provisional Application No. 63/266,932, filed on Jan. 19, 2022, the contents of which are expressly incorporated herein by reference.

FIELD OF THE INVENTION

The present invention relates to devices for delivering an intraocular lens (IOL) into an eye and, more particularly, to IOL injector cartridges that reduce compressive stresses in IOLs while being delivered.

BACKGROUND OF THE INVENTION

A cataract is a clouding of the eye's lens that impairs a person's vision and, if left untreated, causes blindness. Cataracts cause half of all cases of blindness and 33% of visual impairment worldwide. By age 80, more than half of all Americans have cataracts. As a result, each year approximately 1.4 million people in the United States alone undergo cataract surgery, whereby the clouded lens is removed and replaced with an intraocular lens (IOL) implant.

Intraocular lenses (IOLs) are commonly implanted in the eye as a replacement for the natural crystalline lens after cataract surgery. The IOL provides the light focusing function originally undertaken by the crystalline lens. Insertion of an IOL for the treatment of cataracts is the most commonly performed ophthalmic surgical procedure.

A typical IOL includes a disc-shaped optic or lens body for focusing light toward the retina of the eye. In addition, the IOL also includes one or more fixation members or haptics extending outward from the optic for securing and centering the IOL in the desired position within the chamber of the eye. The IOL is implanted directly into the eye through a small incision in a way that reduces trauma and expedites post-surgery healing. To fit through this small incision, modern IOLs are designed to be deformed, e.g., rolled, folded or the like, to a relatively small profile prior to insertion into the eye and then allowed to return to their original shape within the eye.

A useful technique for inserting an IOL into the eye includes use of an IOL injector. Injectors for delivering IOLs into the eye typically employ a syringe-like handpiece and a cartridge having a hollow injection tube or cannula through which the folded IOL is passed using a push rod. The cartridges are often made of disposable materials, such as plastics, and remain in a sterile package until ready for coupling with the handpiece, and may be pre-loaded with an IOL or not.

The cartridge injection tube includes a small diameter distal tip that is insertable into the incision within the eye. A push rod urges the IOL through the injection tube into the eye. The distal end of the cartridge is beveled into a sharp point that enables insertion through the corneal incision and facilitates expulsion and manipulation of the IOL into the capsular bag.

It is advantageous to only make a small incision in the eye when inserting an IOL. Accordingly, an injection tube that tapers to a small diameter tip is typically used. As the IOL progresses down the injection tube, increased force is needed. Many inserters use a screw-type device to advance the push rod for better mechanical advantage, though this involves a stop and start advancement as a proximal dial is rotated and re-gripped by the user in several discreet steps. Also, the IOL or the cartridge tip may be damaged during insertion due to push rod/IOL interaction or high compressive forces. Then, as the IOL is being expelled, the resistant force dramatically decreases. Consequently, the expelled IOL tends to pop open into place within the eye, and there is an increased risk of damaging the eye.

In view of the above, there is a need for a cartridge that requires less force to pass an IOL through and/or will create less compressive stress on the IOL.

SUMMARY OF THE INVENTION

The present application provides an intraocular lens (IOL) injector cartridge for receiving and delivering an intraocular lens having an optic to the inner eye, comprising a main body extending along a longitudinal axis from a proximal opening for receiving the intraocular lens to a distal end which defines a distal opening smaller than the intraocular lens through which the intraocular lenses expelled. The main body may have a narrowing lumen extending from the proximal opening to the distal opening, wherein the lumen further has a discontinuity or step formed in a midsection thereof and extending longitudinally for at least 0.2 cm, such as 0.2-0.5 cm, whereby the discontinuity or step facilitates a stress-optimized spiral rolling-up or folding of the optic of the intraocular lens.

Another IOL injector cartridge disclosed herein has a main body extending along a longitudinal axis from a proximal opening for receiving the intraocular lens to a distal end which defines a distal opening smaller than the intraocular lens through which the intraocular lenses expelled. The main body has a funnel portion with a plurality of axial grooves formed in an outer surface thereof, the axial grooves being spaced apart around the outer surface.

A still further IOL injector cartridge has a main body extending along a longitudinal axis from a proximal opening for receiving the intraocular lens to a distal end which defines a distal opening smaller than the intraocular lens through which the intraocular lenses expelled. The main body has a narrowing lumen extending from the proximal opening to the distal opening, wherein the lumen defines a luminal shape at the distal end which deviates from an oval of equivalent aspect ratio with a tension $\Sigma H$ of 1.2 on top/bottom and a tension $\Sigma W$ of 1.4 on each side. This results in a luminal shape at the distal end of the cartridge which deviates from a standard oval of equivalent aspect ratio such that the luminal shape is larger than the standard oval between equatorial points.

IOLs as disclosed herein may have one or more of the attributes described above.

BRIEF DESCRIPTION OF THE DRAWINGS

Features and advantages of the present invention will become appreciated as the same become better understood with reference to the specification, claims, and appended drawings wherein:

FIG. 2A is a top plan view of the cartridge of FIG. 1, while

DETAILED DESCRIPTION OF THE PREFERRED EMBODIMENTS

Figure 1B:
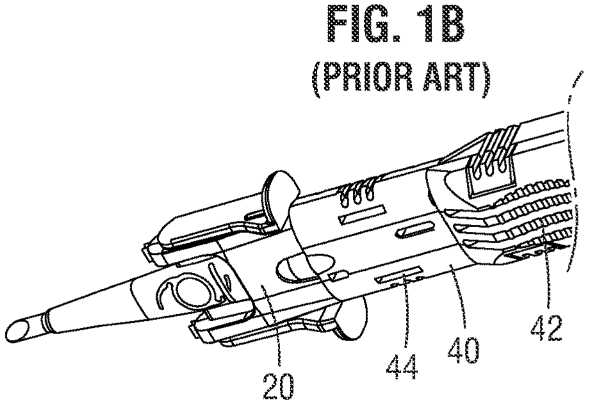
FIG. 1B (PRIOR ART)
FIGS. 1A and 1B are perspective views of a prior art intraocular lens (IOL) cartridge with inserter (partial)
Figure 1A:
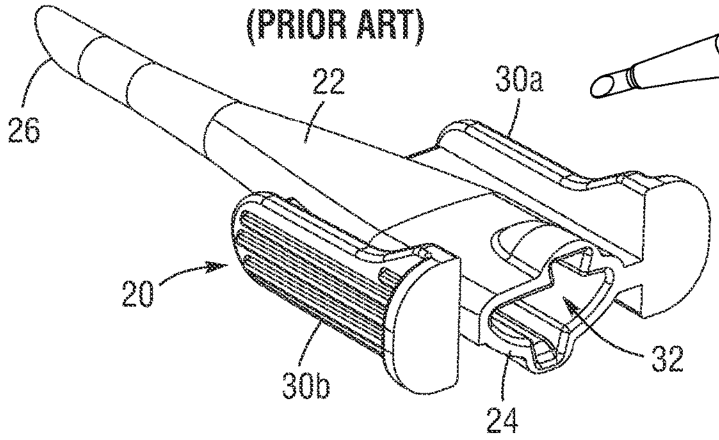
FIG. 1A (PRIOR ART)
Figure 2A:
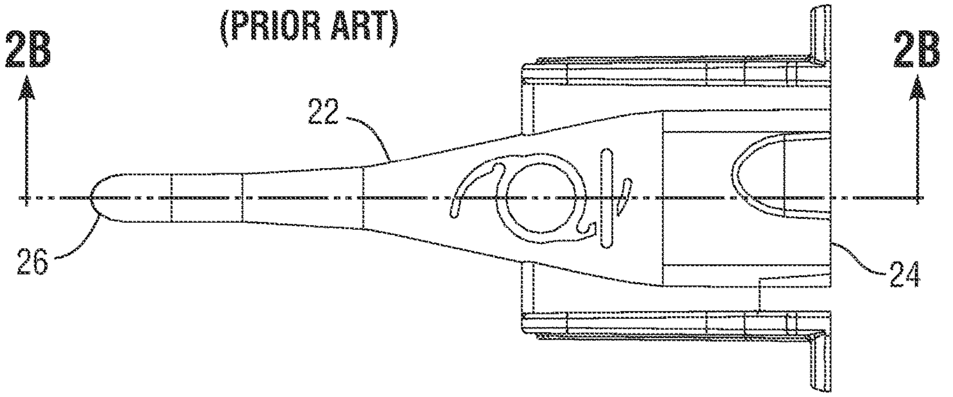
FIG. 2A (PRIOR ART)

FIGS. 1A/1B and 2A/2B illustrate an IOL cartridge 20 of the prior art which includes a main body 22 extending longitudinally from a proximal opening 24 to a distal end 26. A pair of webs project transversely outward from opposite sides of the main body 22 and terminate in generally vertically-oriented finger grips 30*a*, 30*b*. The main body 22 of the cartridge 20 defines a interior wall 31 that defines a gradually narrowing lumen 32 extending longitudinally from the proximal opening 24 to a distal opening 34 (FIG. 2B) at the distal end 26. It should be noted that several views of the cartridge 20, namely FIGS. 1B and 2A, show a side on which is placed an embossed image of an IOL on the exterior of the cartridge main body 22. The image is helpful during an implantation procedure to align an actual IOL being advanced within the transparent cartridge at a particular step in the process.

FIG. 1B shows the cartridge 20 attached to an IOL holding station 40 connected to a handpiece 42 of an injector system. In this version, sold as the TECNIS iTec Preloaded Insertion System by Johnson & Johnson Surgical Vision, Inc. of Santa Ana, CA, the holding station 40 contains a pre-loaded IOL (not shown) within an inner chamber. One or more openings 44 in the holding station 40 are sized to receive a small cannula of a viscoelastic applicator, such as Healon viscoelastic available from Johnson & Johnson Surgical Vision, Inc. Insertion of the cannula and manipulation of the viscoelastic applicator lubricates the inner chamber and folds a trailing haptic over the central disc-shaped optic of the IOL. Details of this structure and procedure are seen in U.S. Pat. No. 8,273,122 to Anderson, which is expressly incorporated herein by reference.

Figure 2B:
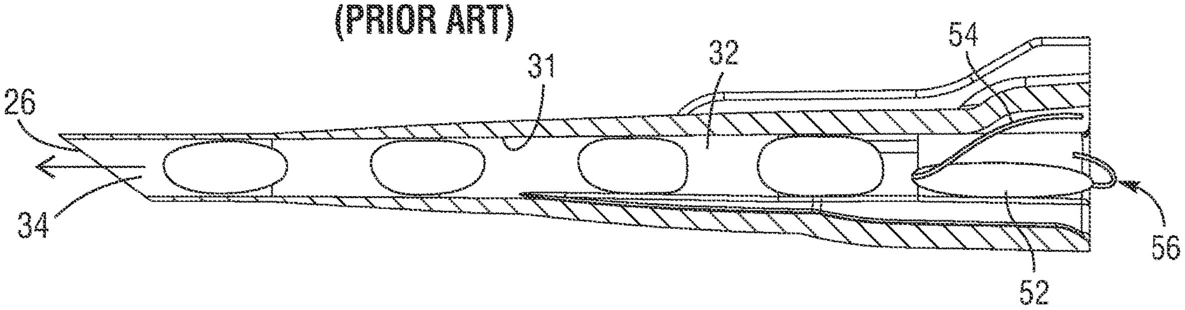
FIG. 2B (PRIOR ART)
FIG. 2B is a longitudinal sectional view through the cartridge illustrating progressive advancement of an IOL therethrough to a beveled distal end.

FIG. 2B illustrates an IOL having a disc-shaped optic 52, a leading haptic 54, and a trailing haptic 56. Typically, the optic 52 has opposed convex faces, although the present invention is not limited to cartridges for any particular type of IOL. The haptics 54, 56 are shown as thin arcuate members extending outward from opposite edges of the optic 52, and generally in the plane of the optic. The haptics 54, 56 curve in the same direction, in this case a counter-clockwise direction looking down on the IOL, as seen by the image imprinted on the cartridge body in FIG. 2A.

FIG. 2B shows the gradually narrowing lumen 32 from the proximal to the distal end of the cartridge 20, and the general shape of the IOL as it progresses through the main body 22. In particular, the gradually narrowing lumen 32 folds, rolls or otherwise compresses the IOL into a small profile so that it may be expelled through the distal opening 34 at the distal end 26 through an incision into the eye. Folding the IOL through the cartridge enables a smaller incision to be used, which helps reduce trauma during the operation and recovery. However, as mentioned, folding and/or compressing the IOL generates significant compressive stresses in the IOL, which is restrained by the surrounding cartridge tube. The outward forces from the IOL against the interior wall 31 of the cartridge which defines the lumen 32 and opposite inward reaction forces from the lumen on the IOL sometimes result in damage to one or the other.

The present application discloses a number of improvements to the prior art IOL cartridge 20, as will be explained. It should be understood that though the improvements are discussed separately in sequence, one or more can easily be combined in one IOL cartridge. Furthermore, the advances inherent in these improvements may be applied to a variety of IOL cartridges other than the illustrated embodiment.

Figure 3A:
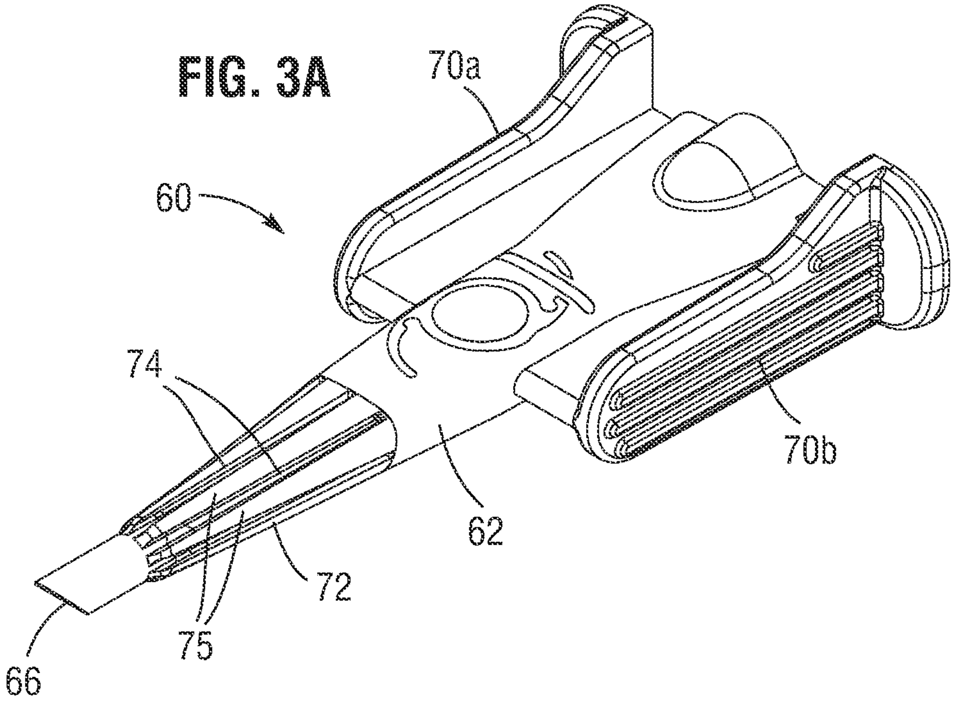
FIGS. 3A and 3B are front and rear perspective views of an exemplary IOL cartridge of the present application.
Figure 3B:
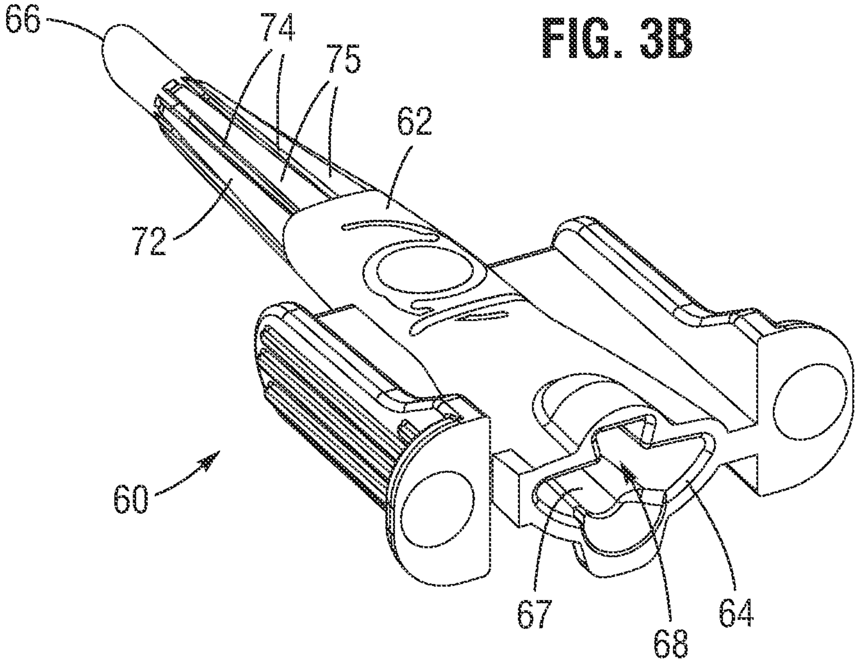

FIGS. 3A and 3B are front and rear perspective views of an exemplary IOL cartridge 60 of the present application which includes a main body 62 extending longitudinally from a proximal opening 64 to a distal end 66. The main body 62 of the cartridge 60 defines a interior wall 67 that defines a gradually narrowing lumen 68 extending longitudinally from the proximal opening 64 to a distal opening at the distal end 66. A pair of webs project transversely outward from opposite sides of the main body 62 and terminate in generally vertically-oriented finger grips 70*a*, 70*b*.

Figures 4A, 4B, 4C, 4D, 5:
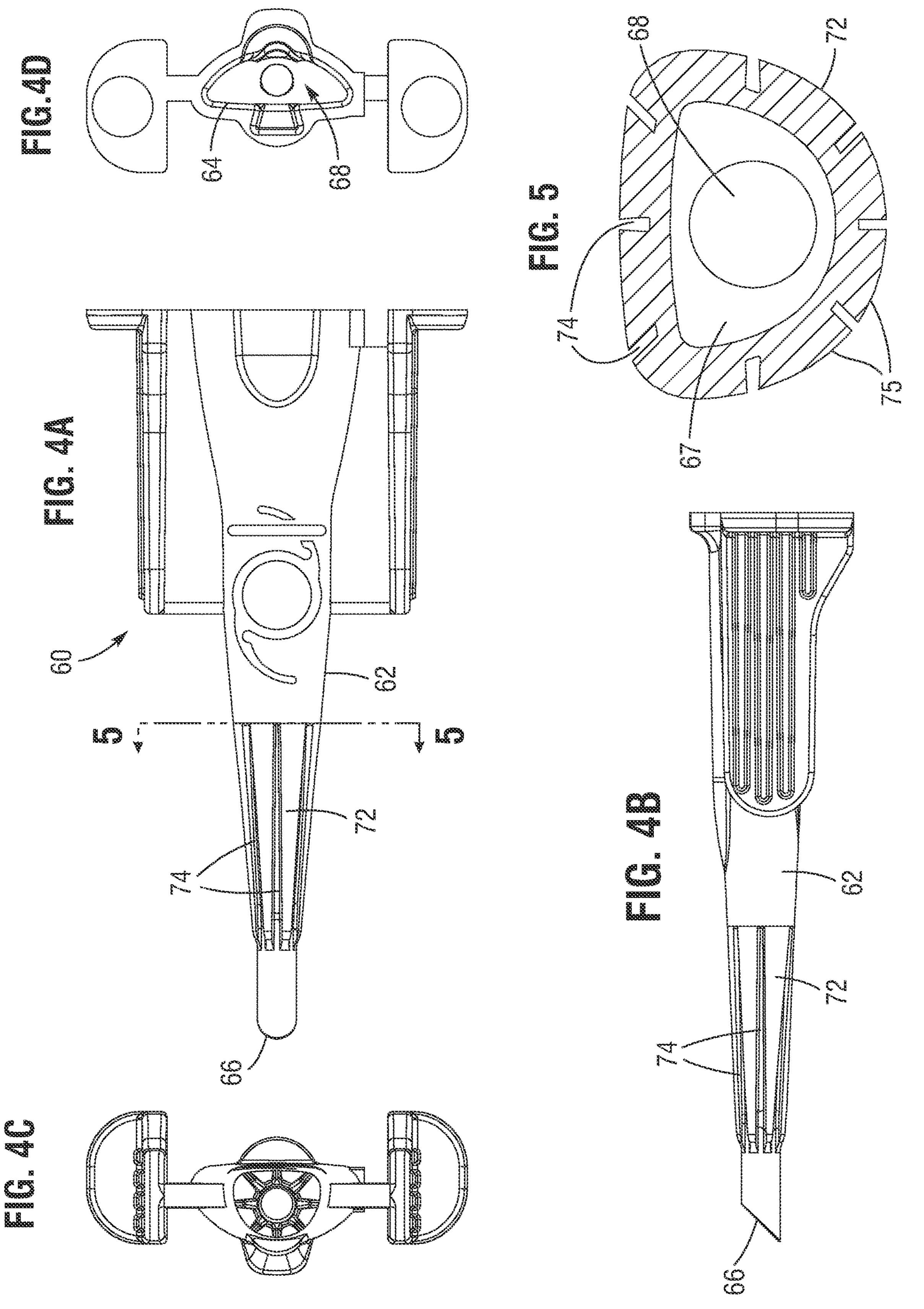
FIGS. 4A-4D are orthogonal views of the IOL cartridge of FIGS. 3A and 3B.
FIG. 5 is a transverse sectional view of a funnel portion of the IOL cartridge of FIGS. 3A and 3B.

FIGS. 4A-4D are orthogonal views of the IOL cartridge 60, and FIG. 5 is a transverse sectional view of a funnel portion 72 of the main body 62. Within the funnel portion 72, the lumen 68 undergoes a majority of the narrowing between the proximal opening 64 and the distal end 66, and as such the IOL is compressed a great deal. The haptics are folded within the optical body. Consequently, the compressive forces build up, leading to an equal and opposite outward reaction force on the wall of the funnel portion 72. To alleviate some of the outward stresses within the wall of the funnel portion 72, a series of axially-oriented channels or grooves 74 between ribs 75 are provided. By removing material circumferentially in this area (in effect, changing a thicker tip to a thinner-walled tip with a series of protruding ribs), the funnel portion 72 has a greater opportunity to flex/remove forces or stress from the IOL.

As best seen in the sectional view of FIG. 5, there are a plurality of axial grooves 74 between axial ribs 75 distributed around the periphery of the funnel portion 72 from an exterior surface inward toward the longitudinal lumen 68. In the illustrated embodiment, there are eight such grooves 74, each of which is generally oriented toward a center of the lumen 68 and angularly spaced apart from the next adjacent groove by 45°. Of course, more or less grooves 74 may be provided, and the distribution need not be evenly spaced. Additionally, each of the grooves 74 extends inward more than 50% of the wall thickness of the funnel portion 72, and preferably between 50-75%. This leaves a small amount of material between the inner end of each of the grooves 74 and the inner luminal wall 68 that act as springs or hinges and permit maximum flexing without compromising structural integrity. The ribs 75 simply splay apart by virtue of being hinged at the grooves 74.

It is also important to note that these are merely examples, and there are many ways to increase the flexural capacity of the funnel portion 72. For instance, a material modification coupled with grooves 74 of lesser depth (e.g., 20% or more of the thickness) of the grooves 74 may also work. Also, non-linear grooves 74 or grooves that are non-uniform around the funnel portion 72 are contemplated. For instance, grooves 74 having a teardrop shape along the axial direction may enable the flexure and thus compressive stresses to be better controlled. Also, any grooves 74 should be contoured to avoid sharp corners which act as stress risers and potential sites for cracking under the highest stresses. Ultimately, one goal is to ensure more uniform flexure along the funnel portion 72 as the IOL passes through, which in turn exerts uniform compressive stress on the lens. Smoothing spikes in such stresses may require a more nuanced shape for the funnel portion 72, and various solutions are possible. 3D modeling and the use of FEA techniques will likely be used to fine tune these flexures/stresses.

The ribbed/grooved funnel portion 72 provides support to the portion of the cartridge experiencing high outward stresses to ensure that there is not excessive flexure resulting in rupture of the material during lens delivery. Though some such flexing could be produced simply by thinning the funnel wall, the risk of rupture is also increased. Moreover, by simply thinning the cartridge wall in the funnel portion 72 a thin-walled mold is required, which would be difficult because of the need for an increase in the packing pressure of the mold. The grooves/ribs in the funnel portion 72 of the cartridge allow the molded material to maintain its ductility in the section of the cartridge in which there is sometimes brittle cracking. It is the increased packing pressure needed to mold a very thin part that induces residual stress in the cartridge, making the tip material more brittle. The ribbed/grooved funnel portion 72 provides flexibility without introducing such negative effects.

Figure 6A:
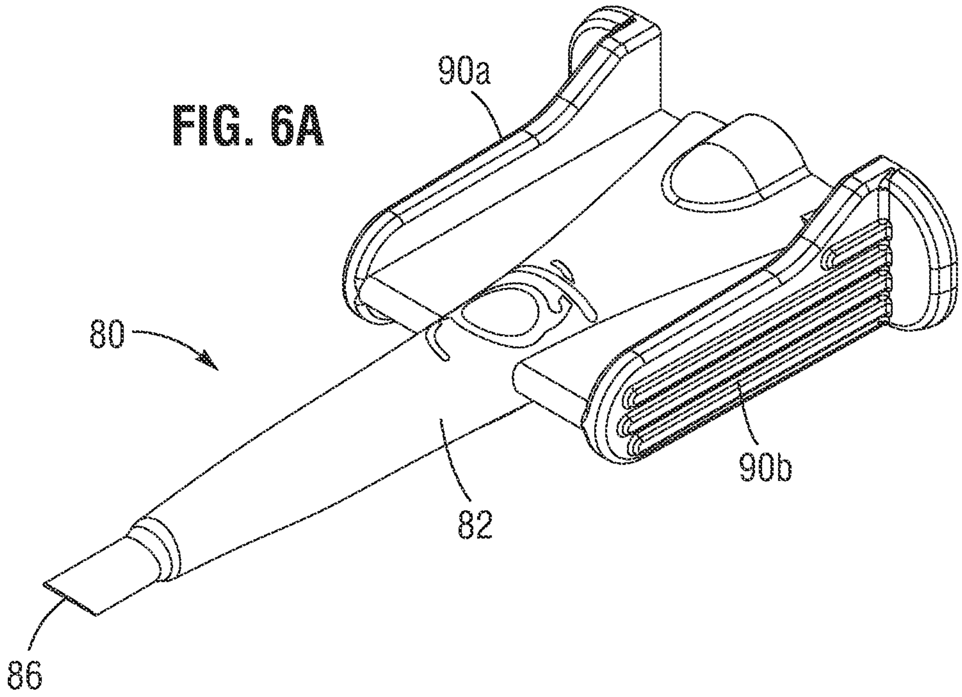
FIGS. 6A and 6B are front and rear perspective views of another exemplary IOL cartridge of the present application.
Figure 6B:
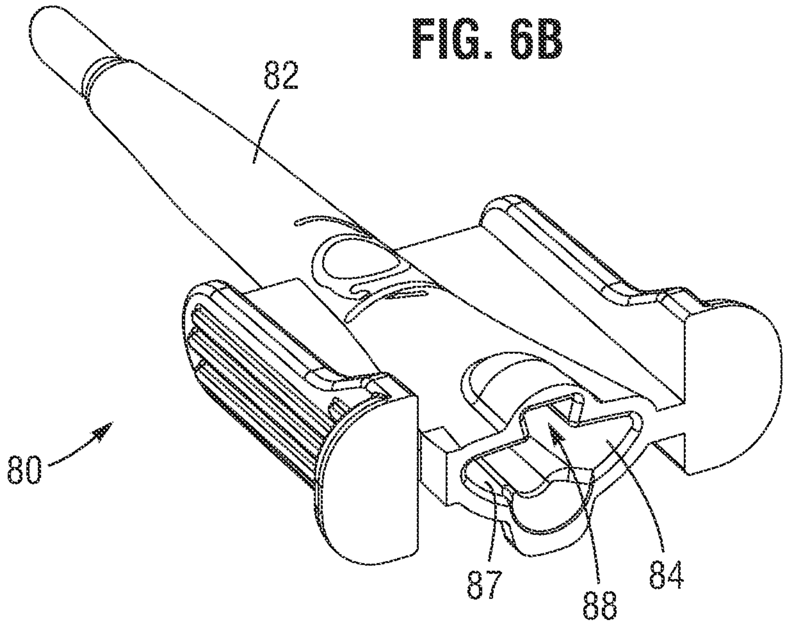

FIGS. 6A and 6B are front and rear perspective views of another exemplary IOL cartridge 80 which includes a main body 82 extending longitudinally from a proximal opening 84 to a distal end 86. The main body 82 of the cartridge 80 defines a interior wall 87 that defines a gradually narrowing lumen 88 extending longitudinally from the proximal opening 84 to a distal opening at the distal end 86. A pair of webs project transversely outward from opposite sides of the main body 82 and terminate in generally vertically-oriented finger grips 90*a*, 90*b*.

Figure 7A:
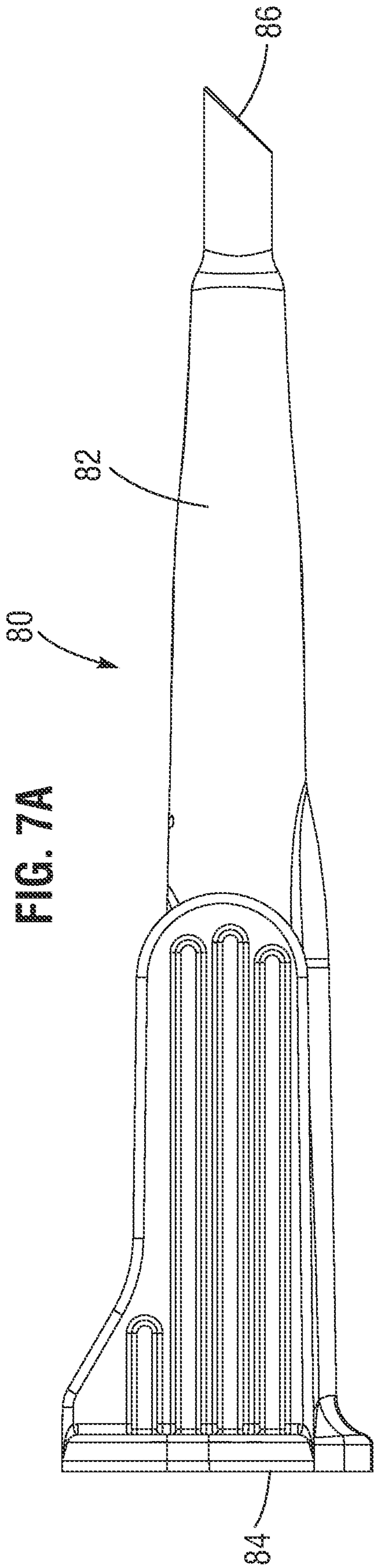
FIGS. 7A-7C are orthogonal views of the IOL cartridge of FIGS. 6A and 6B.
Figure 7C:
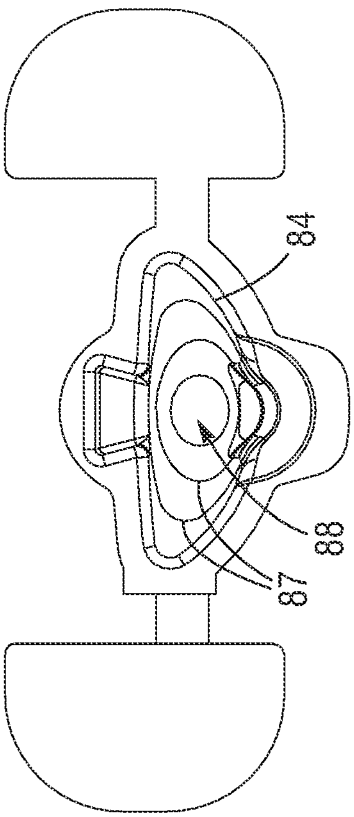
Figure 7B:
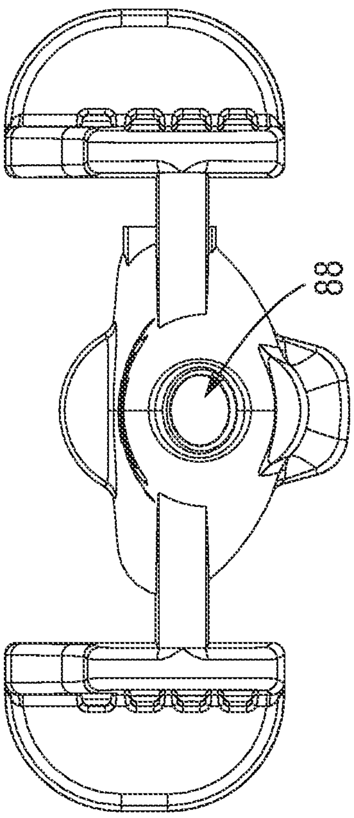
Figure 8:
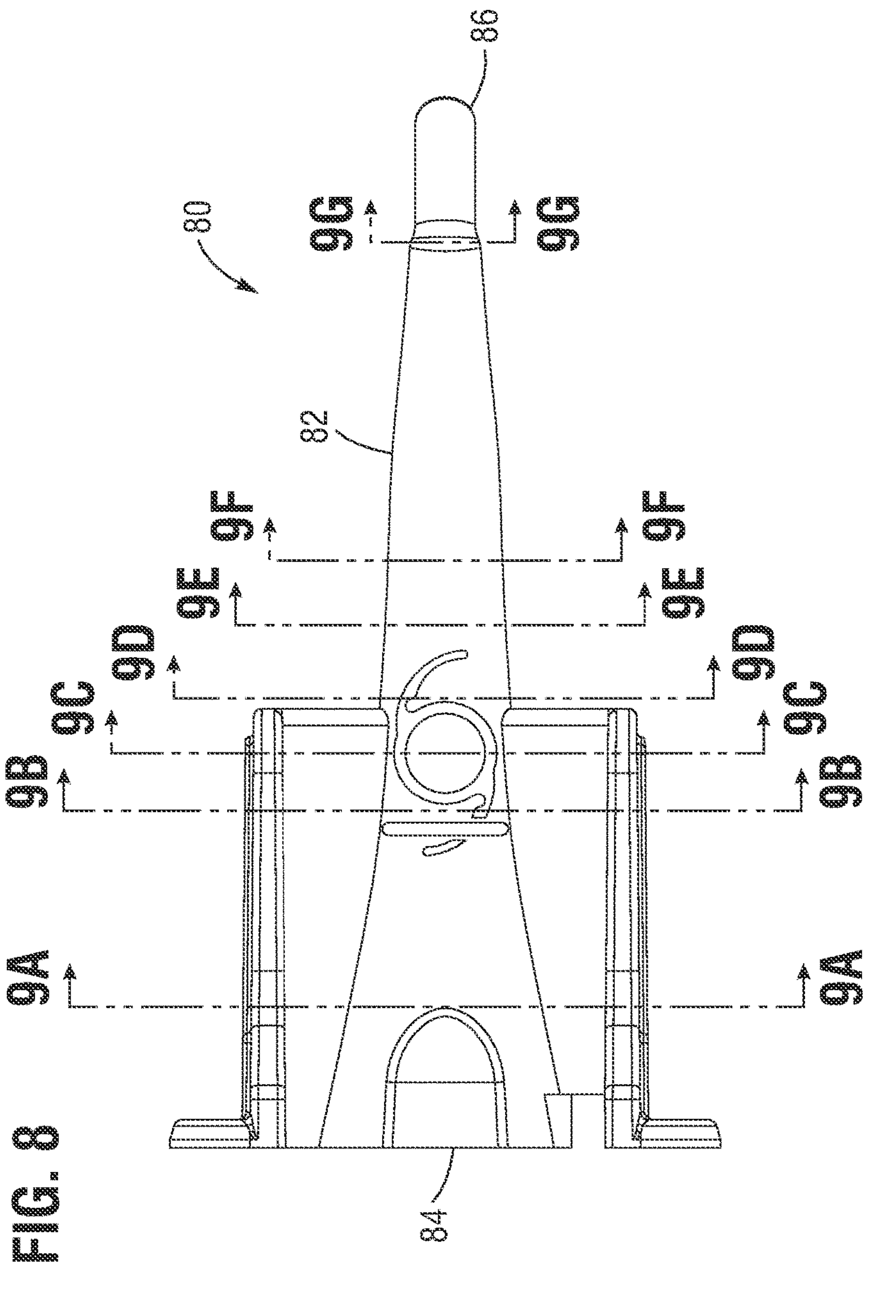
FIG. 8 is a top plan view of the IOL cartridge of FIGS. 6A and 6B.
Figures 9A, 9B, 9C, 9D, 9E, 9F, 9G:
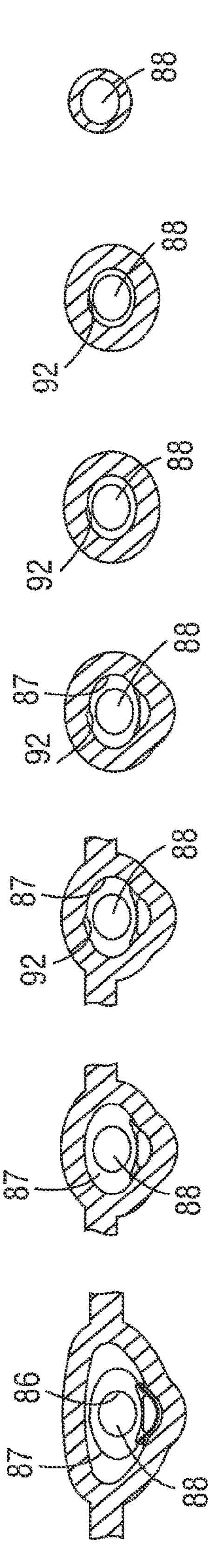
FIGS. 9A-9G are partial and full transverse sectional views of the IOL cartridge of FIGS. 6A and 6B.

FIGS. 7A-7C are orthogonal views and FIG. 8 is a top plan view of the IOL cartridge 80 of FIGS. 6A and 6B. As taken along the progressive section lines in FIG. 8, FIGS. 9A-9G are partial and full transverse sectional views of the IOL cartridge 80 showing a modified inner lumen 88 which reduces stress and helps to fold and IOL passing through the cartridge. In particular, as the interior wall 87 and thus inner lumen 88 begin to narrow as seen in section 9C, a radially small, discontinuity or step 92 begins to form in the otherwise generally oval-shaped lumen. It should be understood that prior art cartridges have narrowing lumens that transition gradually from an oval to a circular distal end. The step 92 starts small, gradually increases in profile, and then after section 9F disappears once again so that the lumen 88 is smooth. The step 92 extends axially along one side wall of the inner lumen for a certain distance, as explained below.

FIGS. 10A-10E are partial and full transverse sectional views of the IOL cartridge 80 of FIGS. 6A and 6B illustrating a progression of an IOL 94 therethrough. These sectional views are positioned roughly the same as the sections having the same alphabetical label as on the preceding page, though sections 10A and 10B only show the main body and a portion of the outward wings. The IOL 94 may be manually placed in the cartridge 80 and is then typically advanced using a plunger and push rod that contacts a rear edge. There are numerous such IOL advancement devices, and the present application encompasses them all.

Figure 10B:
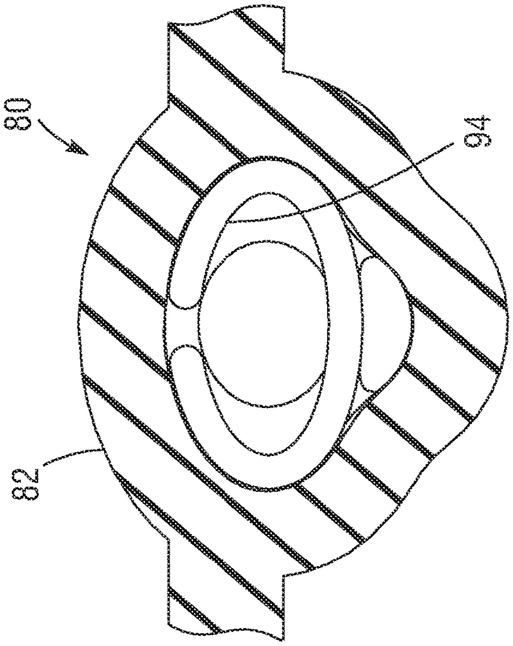
FIGS. 10A-10E are partial and full transverse sectional views of the IOL cartridge of FIGS. 6A and 6B illustrating a progression of an IOL therethrough.
Figure 10E:
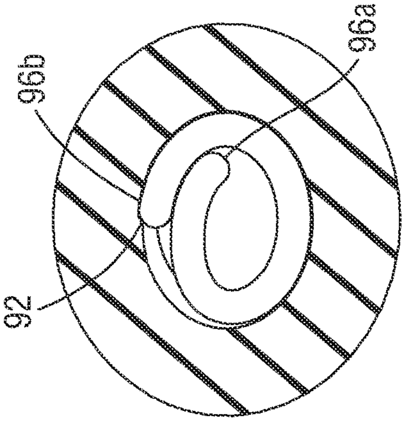
Figure 10D:
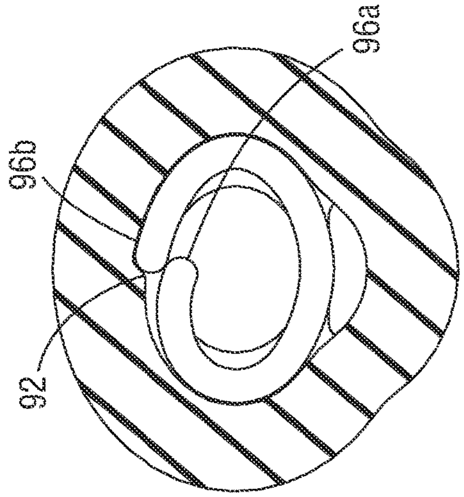
Figure 10A:
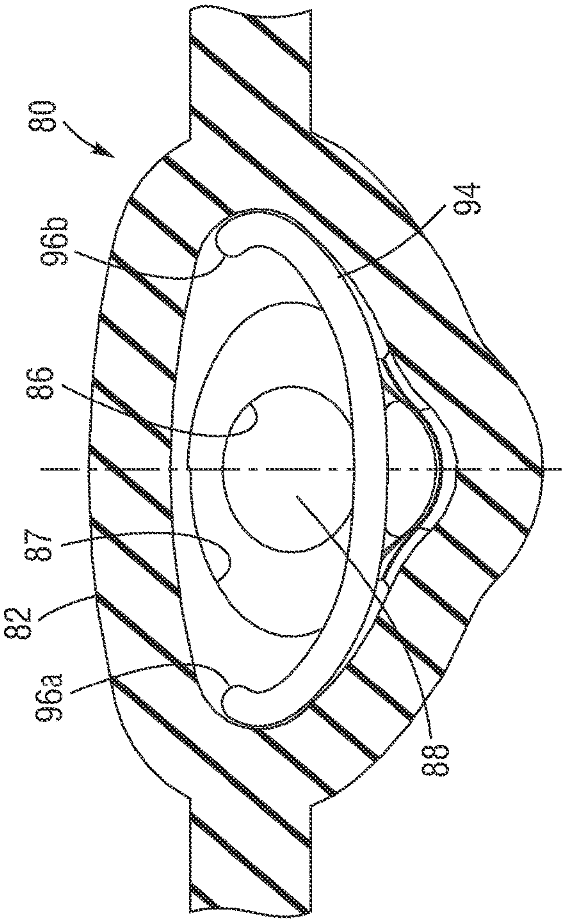

Initially, as seen in FIG. 10A through the main body 82 of the cartridge 80, the optic of the IOL 94 curls around with two free edges 96*a*, 96*b* gradually coming toward each other. Current lens orientation at the proximal opening 84 of the cartridge 80 is as shown, and the haptics (not shown) are located on an anterior side (up). Thus, the orientation of the lens allows for the haptics to be kept folded within the gradually compressing optical body.

FIG. 10B shows a point at which the free edges 96*a*, 96*b* have almost met along the upper wall of the lumen 88 at a central vertical plane through the main body 82. This configuration occurs in many cartridges of the prior art, and further advancement of the IOL through the gradually narrowing lumen 88 causes the free edges 96*a*, 96*b* to abut and compress. The collision of the free edges 96*a*, 96*b* in this manner creates certain stresses within the optic which sometimes causes damage, either to the optic or to the surrounding cartridge body 82. That is, with a smooth inner lumen 88 both free edges of the optic would converge together, eventually binding and then buckling when the lens compressively flexes beyond a threshold. The intent is for the lens to roll into a spiral shape, but MM scanning has shown that more often than not the edges do not slip one over the other. Instead, the lens edges bind, roll inward, and create what looks like the "top of a heart shape" where the edges roll against each other and toward the center until they fully bind; once bound, further compression enforces buckling of the rounded portions of the shape creating three (typically) "petals" of deflection inward with sharp stress areas at the sharpest changes in direction. Such behavior is not controlled and often results in more random lens folding during compression, which creates different lens stresses, different maximum forces to move the lens thru the cartridge, and different interactions between the haptics and lens, none of which are optimal.

Figure 10C:
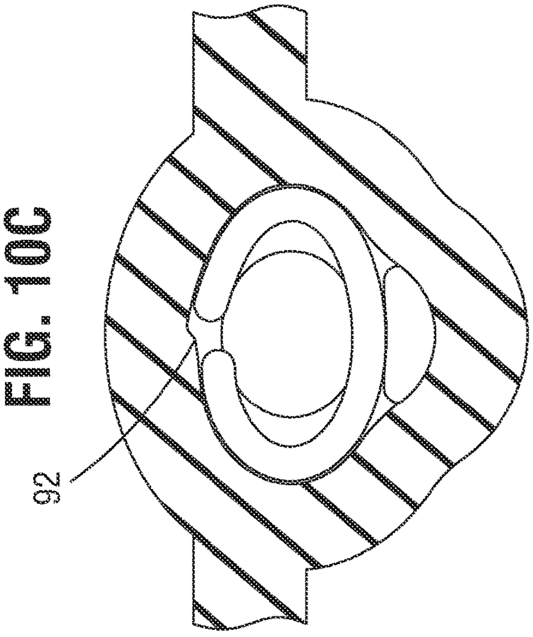

FIG. 10C shows the discontinuity or step 92 commencing in the upper wall of the lumen 88. The step 92 in the illustrated embodiment is formed by the luminal wall 87 becoming higher to the right of the central vertical plane relative to the left of the plane. Subsequently, as seen in FIG. 10D, the step 92 becomes slightly more pronounced and the IOL 94 has been advanced further. This causes a first free edge 96*a* which is to the left of the central vertical plane to cam inward and curl inside or under the second free edge 96*b*, as shown. That is, the step 92 biases one free edge of the optic 94 to tuck or dive under the other free edge and promotes spiral folding as the IOL progresses along the gradually narrowing lumen. Advancing the IOL 94 farther, as in FIG. 10E, causes the optic to continue rolling into a spiral shape while the step 92 gradually recedes in prominence. Ultimately, the lumen 88 resumes a generally oval-shaped profile, and eventually transitions to a circular profile at the distal end 86.

Providing the discontinuity or step 92 thus facilitates folding of the IOL 94 by camming one facing edge underneath the other. Prior art cartridges mostly have inner lumens that are symmetric across the central vertical plane which causes the optic to fold symmetrically about the vertical plane at the mid-section of the optic during the compression stage of delivery. When the free side edges of the IOL come into direct contact, just after section 10B, they briefly cause high compressive forces within the optic. A geometric stiffening of the optic occurs as the opposite side edges of the optic body meet, and this geometric state will increase resistance to further deformation as the plunger rod pushes the optic forward. Modeling indicates that the optic must in fact buckle before it can advance further, leading to a spike in the applied force required to push the optic forward. Typically, one free edges or the other is ultimately forced to fold under, whereupon the IOL continues down the cartridge lumen and is fully folded. However, the high compressive forces at the point at which the free edges contact each other sometimes leads to damage of the optic, such as surface defects, or even damage of the wall of the cartridge. Sometimes, the optic even becomes stuck within the cartridge lumen because of the symmetric folding. Removing this behavior could result in a smoother transition from the optic being held in the flat state to it being full compressed in the inserter tip, and removal of the spike in applied force could enable development of a push style insertion device that would involve a single continuous forward motion for delivery rather than the intermittent stops required in a screw-type device as a dial is rotated and re-gripped by the user in several discreet steps.

Providing a simple surface feature on the internal lumen of the cartridge such as the step 92 provides a positional offset for each edge of the IOL optic, camming one edge inside the other, with one side being biased upwards by approximately 0.1 mm and the other biased downwards by an equal amount. This feature may develop along a longitudinal midsection of the cartridge and then recedes, as will be seen below, such that the proximal and distal segments of the cartridge lumen have a left/right mirror symmetry, but at the point where the optic edges would otherwise meet the feature is present and is at its maximum size with the greatest bias between the left and the right sides. As the IOL progresses beyond this point a spiral folding pattern will be affected in the optic cross-section, and this configuration will remain through the optic compression process while the inserter geometry gradually returns to a left/right symmetric shape.

The discontinuity or step 92 is expected to reduce the peak force that occurs during delivery, possibly enabling a constant linear push style delivery system and potentially reducing strain in the optic to enable a smaller final tip size and thereby a slightly smaller incision in the eye. Additional potential benefits include a reduction in surface damage or tears due to the reduction in localized strain in the regions where the optic folds as well as a reduction of the likelihood of delivery failures.

Figure 11A:
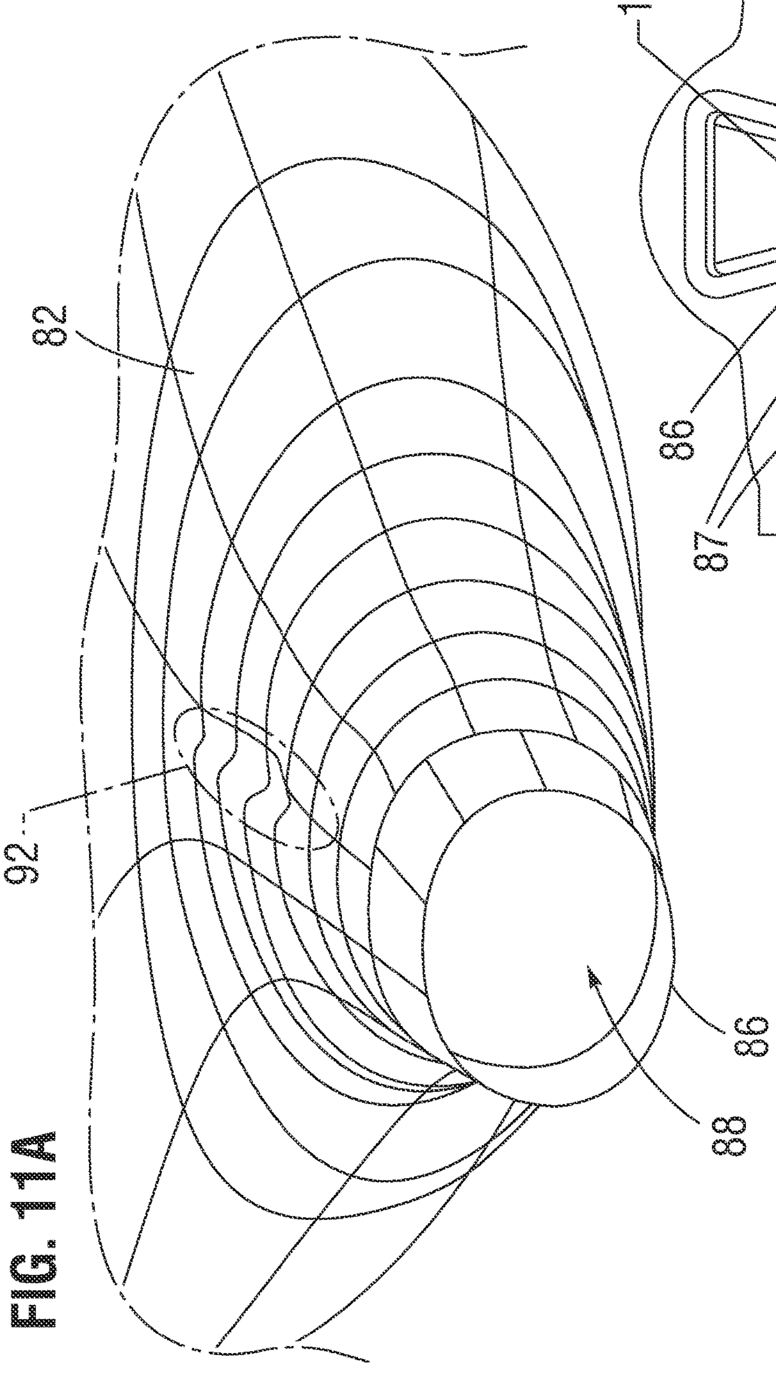
FIG. 11A is a schematic view of the contoured shape of a funnel portion of the IOL cartridge of FIGS. 6A and 6B.
Figure 11B:
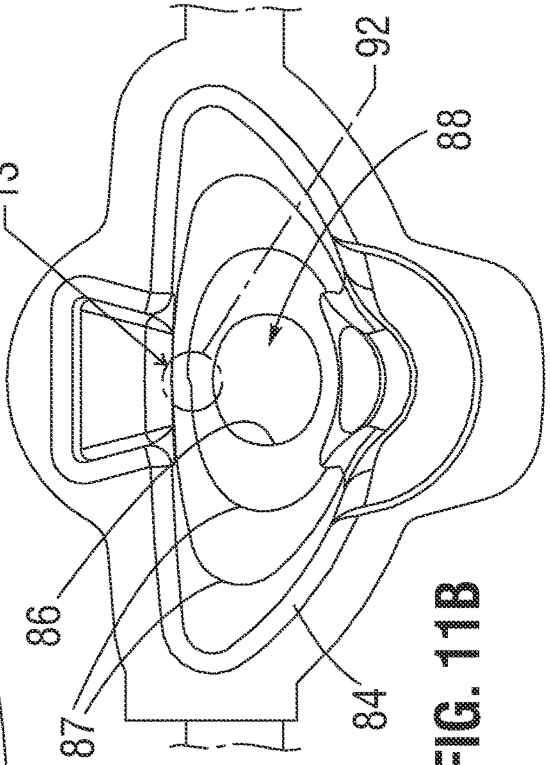
FIG. 11B is an enlarged rear elevational view thereof.
Figure 12:
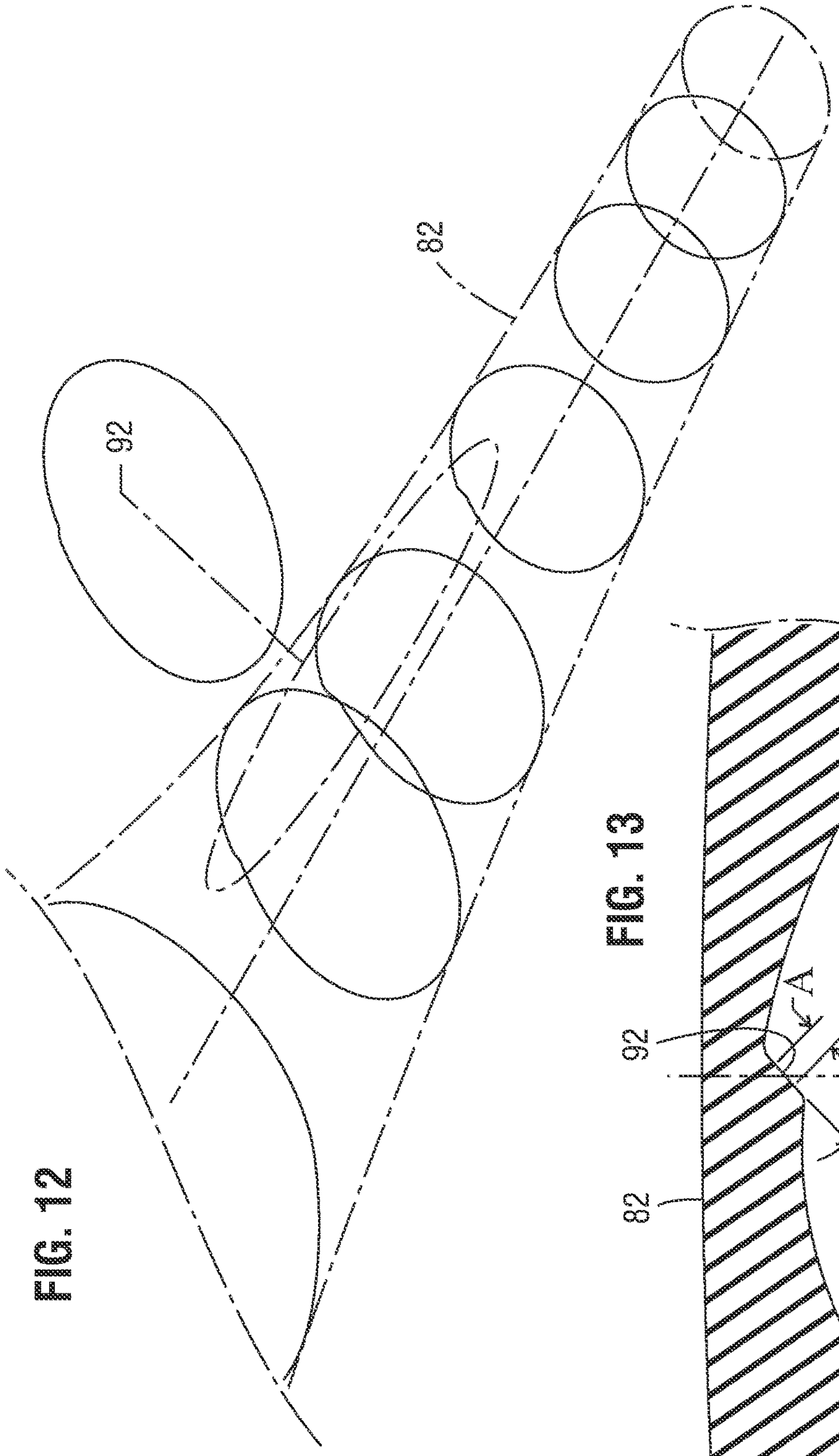
FIG. 12 is another schematic view of the contoured shape of the funnel portion of the IOL cartridge of FIGS. 6A and 6B.

To better illustrate the particular placement of the discontinuity or step 92, FIG. 11A is a schematic view of the contoured shape of a funnel portion of the IOL cartridge body 82, and FIG. 11B is an enlarged rear elevational view thereof. Additionally, FIG. 12 is another schematic view of the contoured shape of the inner step 92. The contour lines shown in both FIGS. 11A and 12 illustrate the narrowing luminal wall 87 and the beginning and end of the step 92 in the "ceiling" of the cartridge lumen 88. It should be understood that the term "ceiling" implies up and down reference directions, and the step is formed in the ceiling because the conventional IOL is inserted into and passes through the cartridge lumen 88 with its free edges upward. Current lens orientation at the beginning of the cartridge lumen 88 is driven by where the haptics are located once the lens is folded—on the anterior face or top of the lens. Thus, the upward curl of the lens allows for the haptics to be kept folded within the lens. However, the rotational orientation of the IOL also determines where the step 92 is positioned, and thus is relative and may vary depending on the particular IOL insertion orientation. In the example shown in FIG. 8, the inner step 92 commences at a location along the gradually narrowing lumen 88 which approximately corresponds to the end of the lateral wings, as seen in FIG. 8, although alignment with any such external feature is not required. The step 92 starts small, increases in size to a maximum, and then decreases and finally disappears and blends in with the otherwise oval-shaped or circular lumen 88. The step 92 extends longitudinally along only a small distance, perhaps a distance of 1 cm or less, and at least 0.2 cm, preferably between 0.2-0.5 cm.

In practice, the step 92 should be approximately the same radial dimension as the thickness of the optic edge, which is larger in lower power lenses. IOL optics are typically biconvex, and thus the thicknesses at the axial center are greater than that at the outer edge. IOL optics have thicknesses at the axial center which typically range between 0.35-0.50 mm (sometimes up to 0.7 mm), and thus the thickness at the outer edge of the IOL optic is less than 0.35-0.70 mm. Accordingly, the radial dimension of the step 92 may be between 0.25 to 0.5 mm. While the present description anticipates that the haptics will be folded within the lens during insertion, the benefits of the inserter geometry described herein could also be recognized if either the leading or trailing haptic, or both, were not contained within the fold of the lens.

Alternatively, the step 92 may be formed by a single cam member that has a relatively short axial profile and acts as a sudden ramp at a location where the side edges of the IOL would otherwise collide head-on. The cam or step 92 must be located where the edges meet, not too soon or too late, or the camming effect will be negligible. The elongated nature of the illustrated step 92 is mainly a constraint of the manufacturing process. The cartridge is injection molded, and thus the internal surface has to have smooth transitions so that a) the material can flow in the mold cavity b) the part can be easily removed from the mold core and c) to avoid complex mold core designs. If other manufacturing techniques are considered such as 3D printing, then the step 92 could be more abrupt and without transitions. For instance, the "step" could be created by halting narrowing on one side of the central vertical plane while the other side continues to narrow. In such a case, the spiral would cause the lens on the side which is not narrowed to move to the outside of the other side.

The start location of the step 92 corresponds to the point at which the IOL optic free edges 96*a*, 96*b* meet, or slightly before they meet, and as such may vary depending on IOL optic diameter and configuration of the cartridge lumen 88. In general, the point at which the free edges 96*a*, 96*b* meet is when the circumference of the cartridge lumen 88 is about equal to a given IOL optic diameter, since the optic rolls upon itself to form a tube. IOL optic diameters range between 6-7 mm, and thus the central point along the longitudinal step 92 is where the circumference of the cartridge lumen 88 is between 6-7 mm. The end point of the step 92 is desirably after the free edges overlap by a minimum amount, such as 1-2 mm or by an angular amount such as 20-45°. Though the preferred start/stop is as described above, the start could be before the free edges abut and the stop could be beyond the overlaps cited.

Figure 13:
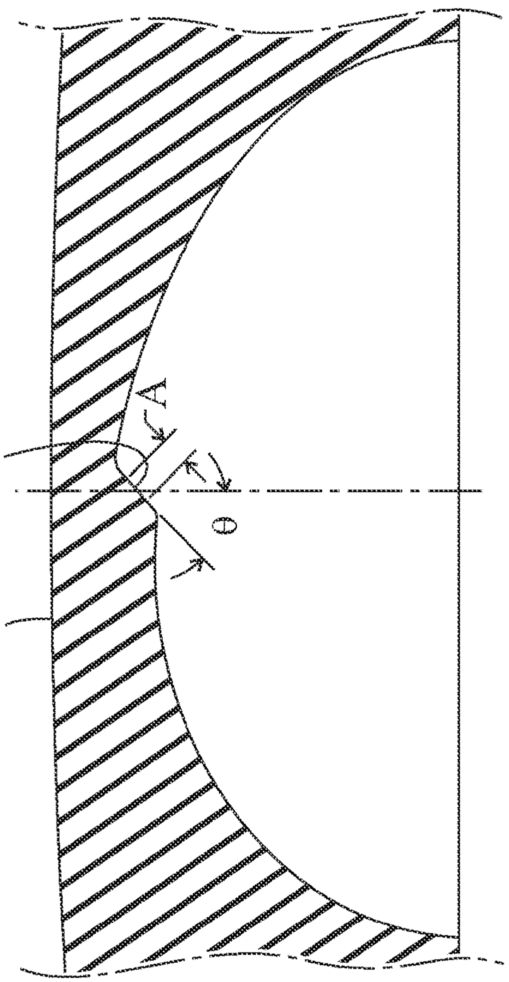
FIG. 13 is an enlargement of an inner step within the funnel portion of the IOL cartridge of FIGS. 6A and 6B taken within the circle 13 in FIG. 11B.

FIG. 13 is an enlargement of the inner step 92 at its maximum prominence taken within the circle 13 in FIG. 11B. The step 92 is desirably formed by an angled transition between the generally oval-shaped lumen 88 as it crosses the central vertical plane. The lumen 88 rises higher on the left side of the vertical plane, as seen, than on the right side, and the two sides are connected by this angled step 92. The step 92 may form an angle θ with the vertical plane of about 45°. The angle θ may vary between 30-60°, and even beyond that range, but shallower angles may not provide enough of a ramp and sharper angles may even impede the folding. The angled step 92 connects with the adjacent sides of the lumen 88 at rounded corners, and may have a planar land in the middle that extends a dimension A. This dimension A may be only a fraction of the total height of the stop. In some examples, the dimension A ranges from 0.05-0.2 inches. In some examples, dimension A ranges from 0.75-1.0 inches. In one example, dimension A is about 0.08 inches. Alternatively, the angled step 92 may be formed by a continuously curved "S" or serpentine shape without any planar portions. As the polymer cartridge 80 is desirably injection molded, the angled step or serpentine discontinuity 92 is easily formed on the inner lumen 88. One skilled in the art will be able to select an angle θ that would be most suitable for an individual lens based on parameters including, but not limited to, lens geometry and mechanical properties of the lens.

In addition to reducing stresses and strains during IOL folding in the middle of the cartridge, it is important to also do so at the extreme distal end of the cartridge tip where the IOL is compressed to its maximum amount. During the process of inserting an IOL the optic is compressed through a small injector tip before delivery into the eye. The lens shape is biconvex in cross-section and typically inserter cross-sections are circular, which may result in significant variation in localized strain across the cross-section. The inventors have determined that there may be an optimal cross-sectional shape for the inserter such that strain across the lens when the lens is fully compressed in the tip is normalized across the cross-section.

Strain is a unitless expression, and in terms of strain on an IOL lens within a cartridge, a positive value means parts of the lens bulk are being stretched apart whereas a negative value means they are being compressed. Ideally, as a lens is pressed into a narrowing inserter tip, all regions of the lens will be undergoing compression and have negative strain. Instead, it has been found that some regions are in fact undergoing a stretching force, or tension. That is, strain is not all compressive and certainly not uniform across the lens midsection in a round lumen. Consequently, an inserter geometry that provides a more even strain distribution, where no parts of the cross-section are in a state of tension, is desirable.

Figure 14:
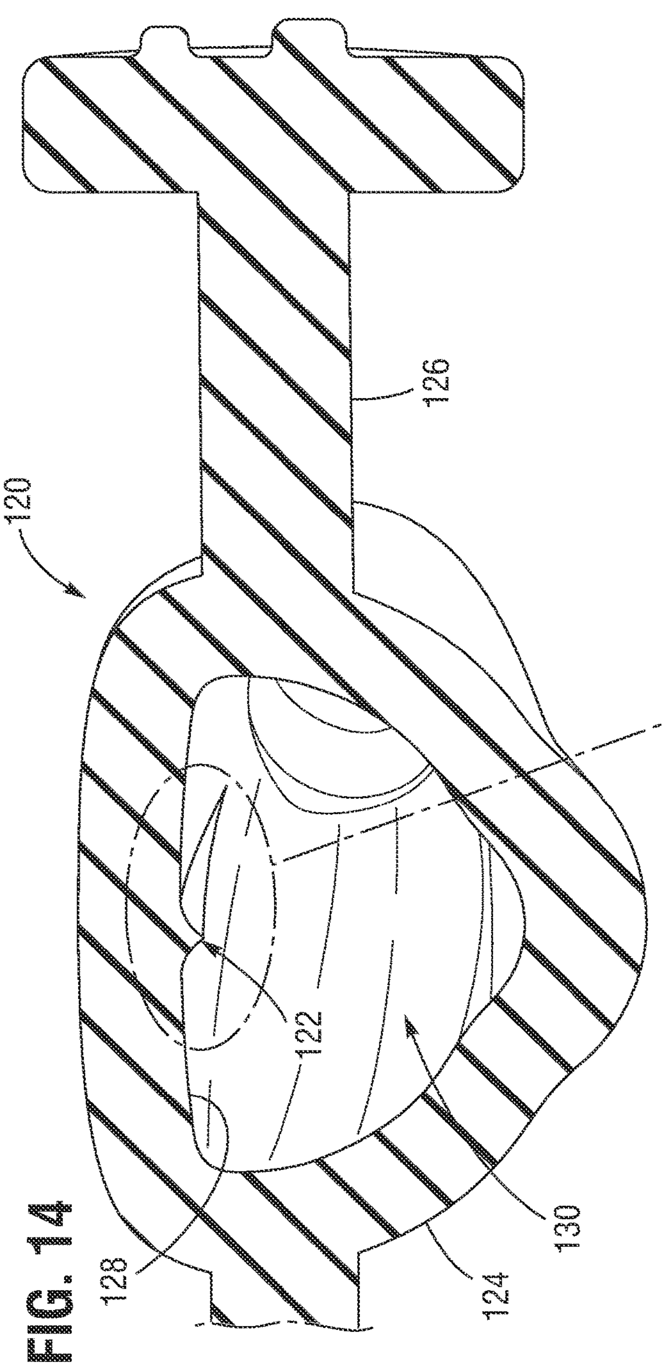
FIG. 14 is a partial transverse sectional view of an alternative IOL cartridge having a modified internal step that facilitates IOL folding.
Figure 14A:
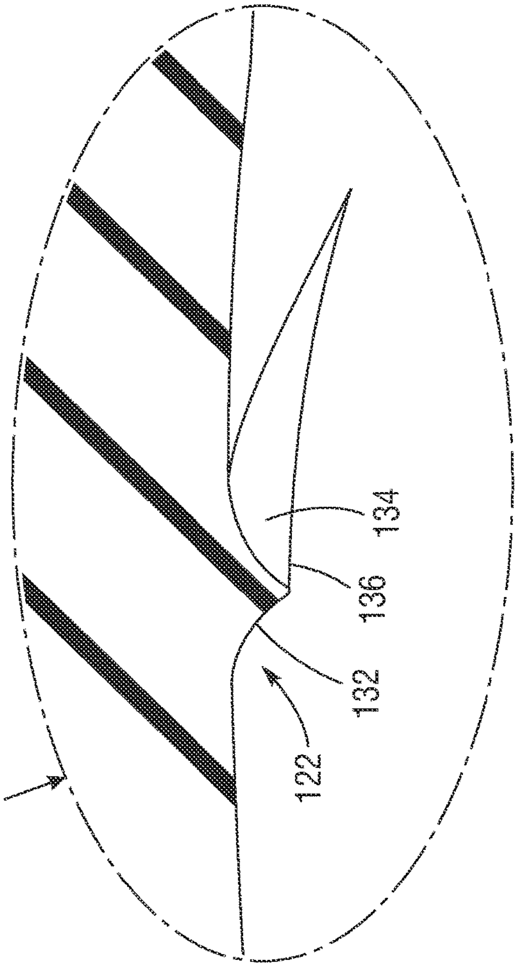
FIG. 14A is an enlarged view of the step.

FIG. 14 is a partial transverse sectional view of an alternative IOL cartridge 120 having a modified internal discontinuity or step 122 that facilitates IOL folding, and FIG. 14A is an enlarged view of the step 122. The IOL cartridge 120 may be similar to the cartridge 60 described above, with a main body 124 extending longitudinally from a proximal opening to a distal end (not shown), and having a pair of webs 126 projecting transversely outward from opposite sides of the main body 124 and terminate in generally vertically-oriented finger grips, as before. The main body 124 defines an interior wall 128 that defines a gradually narrowing lumen 130 extending longitudinally from the proximal opening to a distal opening at the distal end.

The discontinuity or step 122 is again formed in the interior wall 128, projecting inward in generally oval-shaped lumen 130. The step 122 is formed as a V-shaped rib that extends longitudinally along the wall 129, gradually decreasing in profile until it disappears once again so that the lumen 130 is smooth. The step 122 extends axially along one side wall of the inner lumen 130 for a certain distance, with a minimum of at least about 0.2 cm More particularly, the step 122 includes two curved faces 132, 134 on each side of an apex ridge 136. The step 122 may commence suddenly, and have a front or leading end transverse to the longitudinal axis through the cartridge 120, or the step may begin gradually such that the apex ridge 136 increases in size from nothing to a maximum, and then decreases as shown moving distally through the lumen 130. The two curved faces 132, 134 facilitate folding or curling of the IOL edges as the IOL is pushed through the cartridge 120, as described below with respect to FIGS. 15A-15D. In the illustrated embodiment, the V-shaped step 122 is formed on an upper portion of the interior wall 128 as illustrated, though the location is determined by how the IOL is oriented as it passes through the lumen 130, with the IOL lens edges coming together at this upper point.

FIGS. 15A-15D are partial and full transverse sectional views of the IOL cartridge 120 of FIG. 14 illustrating a progression of an IOL 140 therethrough. These sectional views are positioned roughly the same as sections 10B-10E in the earlier embodiment. The IOL 140 may be manually placed in the cartridge 120 and is then typically advanced using a plunger and push rod that contacts a rear edge. The IOL 140 may be provided by the manufacturer preloaded in the cartridge 120 and is be advanced by a medical professional using a plunger and push rod that contacts a rear edge. There are numerous such IOL advancement devices, and the present application encompasses them all.

Figure 15A:
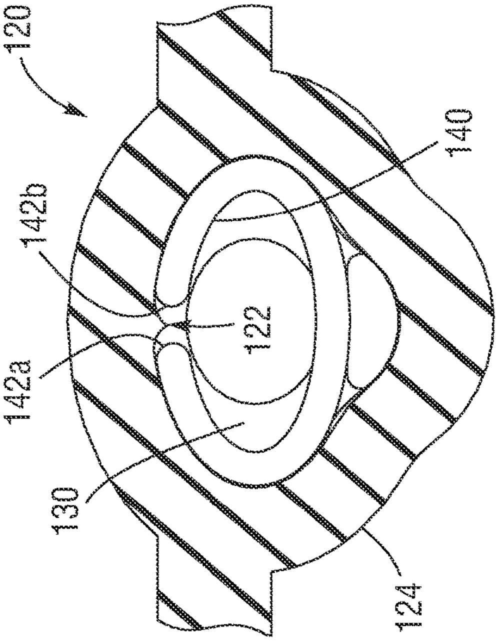
FIGS. 15A-15D are partial and full transverse sectional views of the IOL cartridge of FIG. 14 illustrating a progression of an IOL therethrough.

Initially, as seen in FIG. 15A through the main body 124 of the cartridge 120, the optic of the IOL 140 curls around with two free edges 142*a*, 142*b* gradually coming toward each other. A traditional lens orientation of the cartridge 120 is as shown. The lens haptics (not shown) may be positioned to be folded by the cartridge on an anterior side (up) of the lens. Such an orientation of the lens allows for the haptics to be kept folded within the gradually compressing optical body. Alternatively, the cartridge may be designed where one or more of the leading or trailing haptics may not be folded within the gradually compressing optical body.

FIG. 15A shows a point at which the free edges 142*a*, 142*b* have almost met along the upper wall of the lumen 130 at a central vertical plane through the main body 124. This configuration occurs in many cartridges of the prior art, and further advancement of the IOL through the gradually narrowing lumen 130 causes the free edges 142*a*, 142*b* to abut and compress.

Figure 15B:
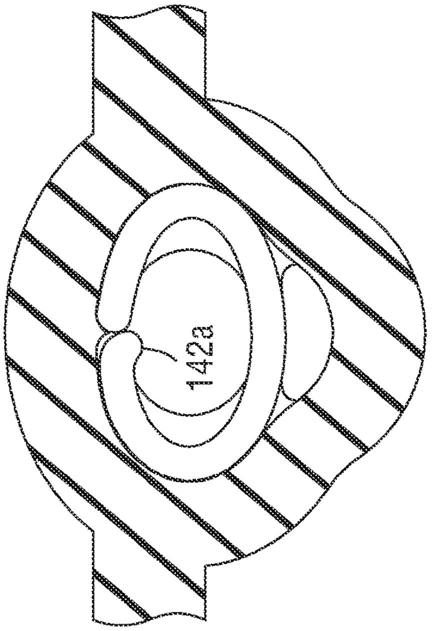
Figure 15C:
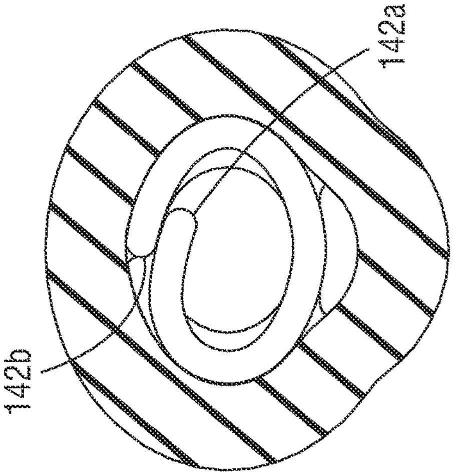
Figure 15D:
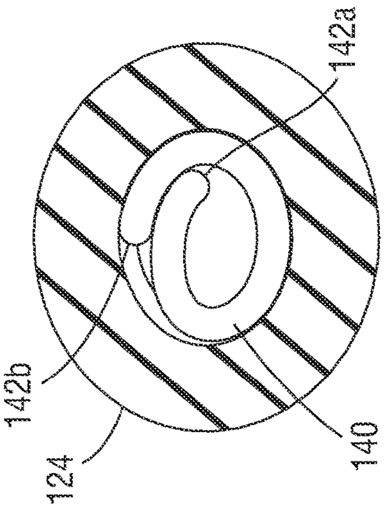

FIG. 15B shows the free edges 142a, 142b reaching the discontinuity or step 122 in the upper wall of the lumen 130. The step 122 is formed as a V-shaped rib with curved faces, and as seen a first free edge 142a which is to the left of the central vertical plane starts to cam inward and curl inside or under the second free edge 142b, as shown. That is, the step 122 biases one free edge of the optic 140 to tuck or dive under the other free edge and promotes spiral folding as the IOL progresses along the gradually narrowing lumen. Advancing the IOL 140 farther, as in FIGS. 15C and 15D, causes the optic to continue rolling into a spiral shape while the step 122 gradually recedes in prominence. Ultimately, the lumen 130 resumes a generally oval-shaped profile, and eventually transitions to a generally circular profile at the distal end, as described above.

The V-shaped step 122 may be symmetric such that the two curved faces 132, 134 on each side of an apex ridge 136 are identical in size and shape. However, to facilitate a first edge 142a folding under the second edge 142b, the left-hand face 132 is preferably steeper in angle than the right-hand face 134 so that the first edge 142a is cammed inward sooner, and dives under the second edge 142b. A similar result may be achieved by positioning the step slightly off-center. That is, the step 122 is symmetric or asymmetric in shape, and centered at the vertical midline or positioned off-center. Likewise, the slopes of each face 132, 134 may be planar, for a V-shaped step 122, or convexly curved for a more wave-shaped step. The term midsection as used herein may be read as referring to the general area at or near the vertical midline.

The illustrations show the second edge 142b essentially remaining in place at the point at which the edges abut, with all folding movement due to further movement of the first edge 142a. This is due to compressive forces within the lumen 130, and may change depending on the particular geometry of the step 122 or other factors.

Figure 17:
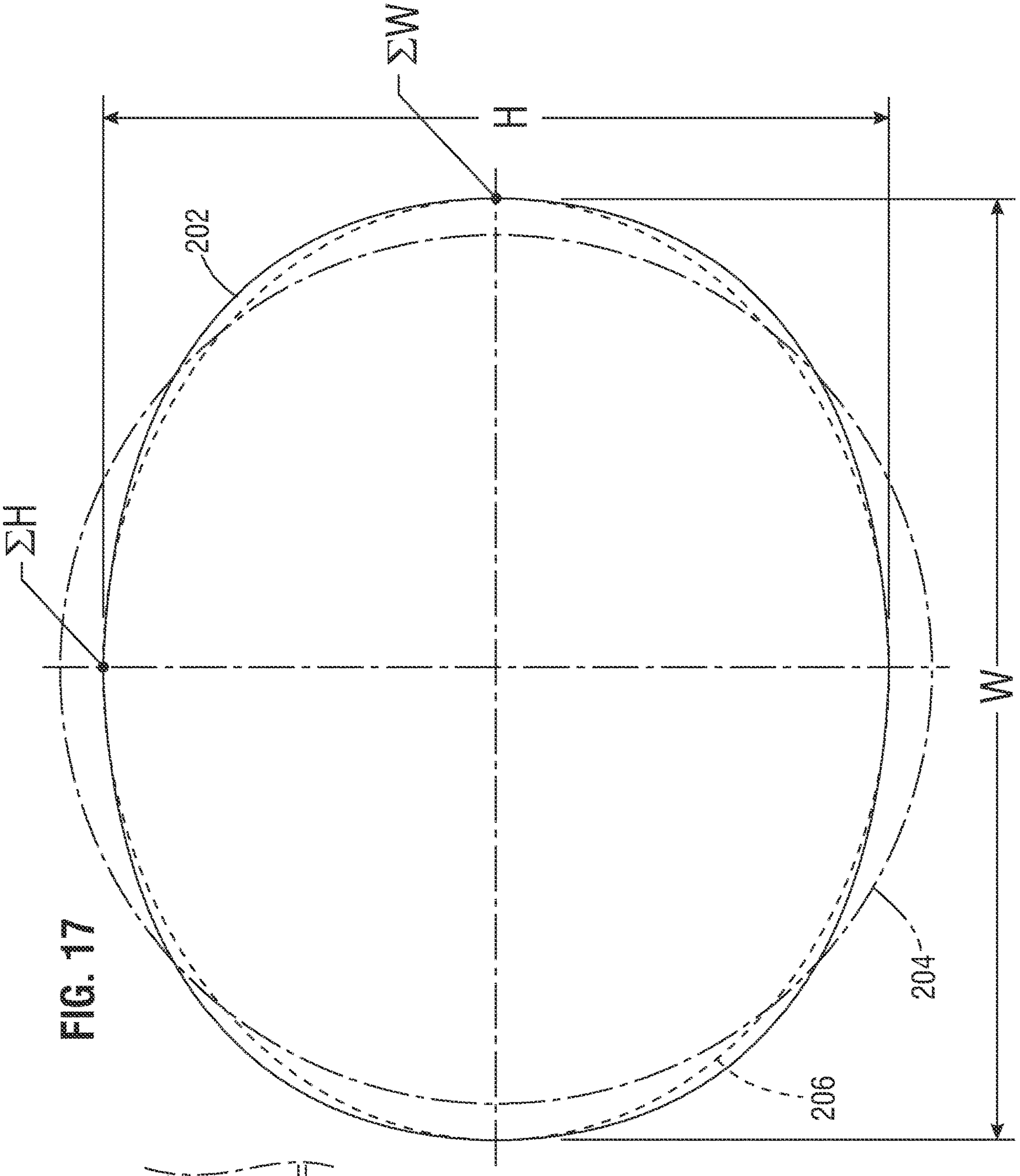
FIG. 17 is a diagram illustrating a luminal shape of the IOL cartridge distal end of FIG. 16 having a preferred geometry.
Figure 16:
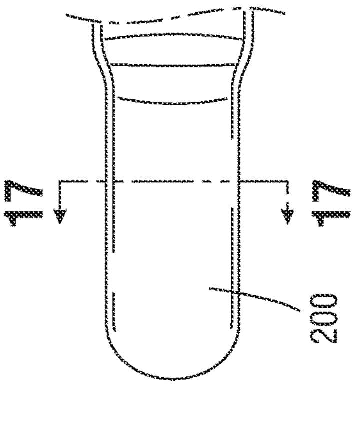
FIG. 16 is a cutaway view of a distal end of an IOL cartridge of the present application.

FIG. 16 is a cutaway view of a distal end of an IOL cartridge 200 of the present application, and FIG. 17 is a diagram illustrating a preferred luminal shape of the distal end. The preferred shape is non-circular and non-elliptical which may normalize strain across the cross-section of a lens when fully compressed. This cross-sectional shape was determined by performing a series of simulated experiments to evaluate minimum and maximum strain and shear levels across a lens cross-section after compression into a geometry of the current configuration, selecting the case with the least variation, and repeating another experiment around this local minimum.

It should be noted that the desired shape as in section FIG. 17 may be implemented gradually before full compression of the IOL—for example, phased in gradually along the length of the inserter until this section. The IOL essentially transitions to this shape as it moves forward though the cartridge 200 and is gradually compressed more and more. The final non-circular and non-elliptical shape is reached at or near the narrowest lumen portion towards the distal tip of the cartridge 200 where the compressive forces are the greatest.

The process was to create an ellipse with an aspect ratio and then add an additional degree of freedom by allowing the curve to deviate (i.e., expand) from this construction curve in each quadrant. The aspect ratio is the proportion of the horizontal to the vertical dimension of the cross-section along the equatorial axes. The aspect ratio of the ellipse was first optimized, and then the final curve was created with a spline fixed to be tangent to the ellipse where it intersected with the horizontal and vertical axes but could deviate between those two points based on a start and an end tension. The cross-sectional shape was created in a SolidWorks CAD application as a parametrically defined set of four curves (ellipse quadrants) created with a spline with defined tensions on the top and side having start and end points coincident with the quadrants of the ellipse with a specified width and aspect ratio. This curve was then mirrored horizontally and vertically to create the final cross-sectional shape that was swept to create the internal geometry of the inserter. For any given aspect ratio and set of tensions the width of the tip was modified such that the internal cross-sectional area would match that of the nominal current inserter design. These parameters can represent a broad range of shapes, a subset of which includes circles and ellipses.

Evaluation of the nominal case and each design contender was performed with a simple 2-D plane stress finite element model in an MSC Marc Mentat application, where the lens cross-section was shrunk with a thermal load and then expanded back to the nominal size inside the constraint of a tip having the internal shape of the current design. The sidewall thickness was constant and equal to that of the nominal design. Both the major principal strain and the maximum principal shear value of strain were used as the optimization goals, the range and absolute maximum value of each was to be minimized.

The nominal circular case, with a 1.46 mm diameter and 1.67 $mm^2$ cross-sectional area, showed a substantial variation in strain across the cross-section when a biconvex lens of approximately the same cross-sectional area as a current 20 diopter Tecnis IOL was compressed to fill it. It is believed that in an ideal situation the strain would have been consistent, with all sections of the lens under equal compressive strain. However, the major principal value of elastic strain was found to range from −0.486 to +0.813. That is, portions of the cross-section were placed into a state of tensile rather than compressive strain, and this effectively lessened the efficiency of the compression. The shear strain varied from 0.097 to 0.619.

After an optimization process using SolidWorks, as explained above, a cross-sectional shape was determined that resulted in a strain variation of −0.485 to −0.216, meaning that all portions of the lens were under compressive strain and the total range of strain had been reduced by approximately 80%. The peak shear strain was reduced substantially to 0.39, with a range of 0.012 to 0.39 representing a 35% reduction. This optimal shape had a width of 1.57 mm and a height of 1.31 mm (aspect ratio 1.2), a side tension of 1.4 and a top tension of 1.2. Again, these tensions are used to define in SolidWorks a spline curve relative to a regular elliptical shape. Of course, the ranges of aspect ratio, tensions or the size and position of the discontinuity may differ while still realizing relatively even compression and no tension. Therefore, an aspect ratio in the range of about 1.1 to 1.3 is believed suitable. Higher diopter lenses might perform better at an aspect ratio just above 1.4, however the surgeon needs to retain the ability to rotate the cartridge tip inside the wound without creating any additional stretching from a tip that is wider than it is tall. A higher aspect ratio might lead to more stretching in this case and therefore may not be preferable. Further, extending the range below 1.1 would not result in significant benefits as the geometry becomes functionally identical to a circular cross-section.

A graphical representation of one proposed geometry is seen in FIG. 17. The proposed transverse cross-sectional shape of the tip 200 has a solid contour at 202. This is shown superimposed over a regular circle 204, and a standard ellipse or oval 206 with the same aspect ratio, or width to height. As is well known, an ellipse or oval is defined such that the sum of the distances from any point on the curve to two fixed points (the foci) is a constant. The preferred contour 202 intersects and is tangent to the curve of the oval at the four equatorial points along the horizontal and vertical central axes, as seen, but deviates from the oval in between. In particular, the contour 202 expands outward in the chordal sections between the equatorial points. The geometry of the contour 202 deviates from an ellipse of same aspect ratio with a tension ΣH of 1.2 on top/bottom and a tension ΣW of 1.4 on each side, again, created using SolidWorks software.

Figure 18:
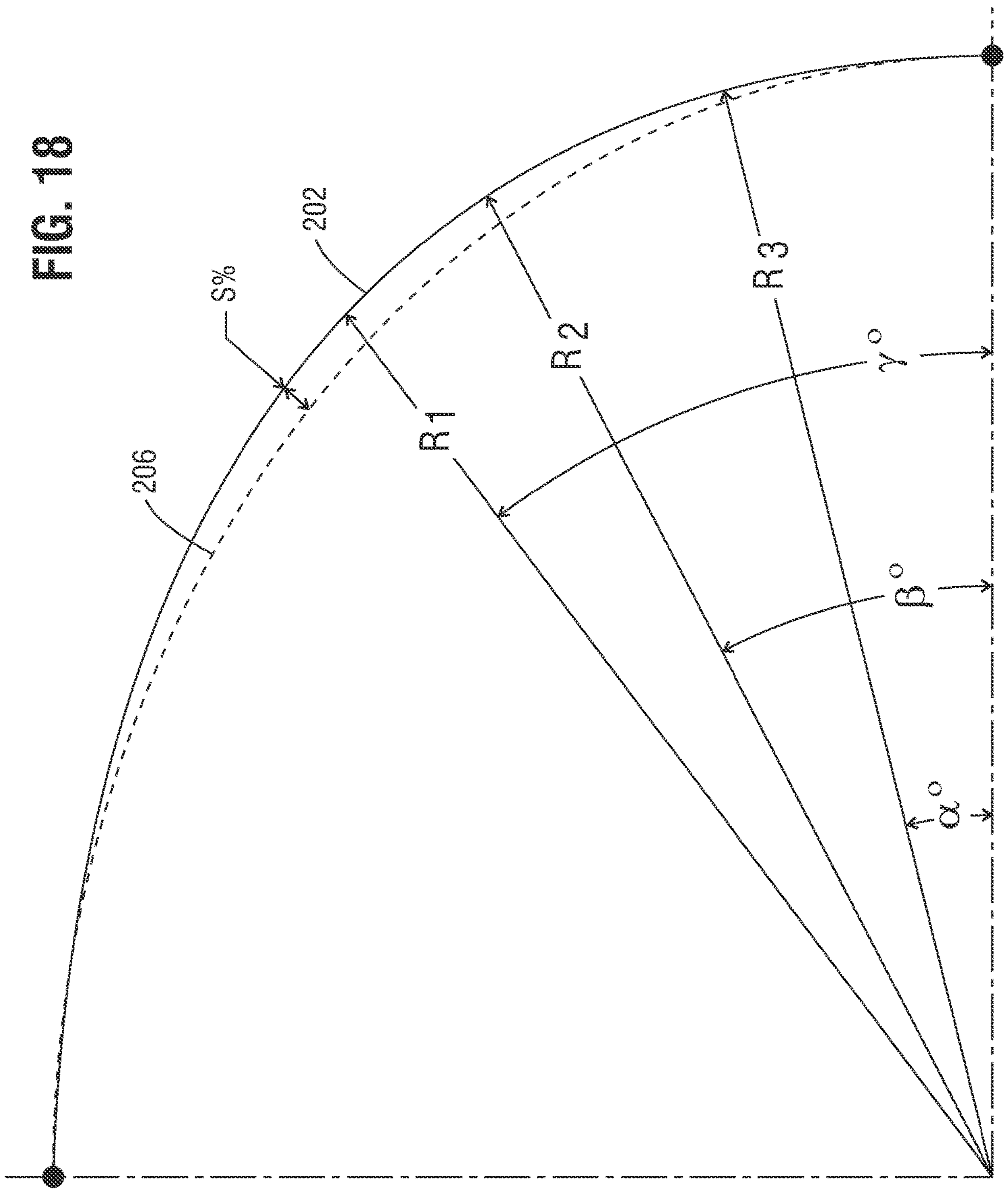
FIG. 18 is a detailed view of one quadrant of the luminal shape of the IOL cartridge end tip of FIG. 17.

After testing using the finite element model as explained above, more uniform stress in the simulated lens was seen with certain modified ovals. The modification is perhaps best expressed by looking at one quadrant of FIG. 17, as shown in FIG. 18. The expanded modified oval 202 is seen superimposed on a regular oval 206. The two curves intersect and are tangent to each other at the equatorial points along the major and minor axes, but in between, the modified oval 202 expands outward. Three "radii" $R_1$, $R_2$ and $R_3$ are drawn from the center of the oval to the modified oval 202 at angles from the horizontal α°, β° and γ°. These are not strictly speaking radii because the curvatures along the quadrant arc are by definition never centered at the center of the oval. However, these "radii" $R_1$, $R_2$ and $R_3$ are useful to describe the variance from the standard oval 206. Namely, the modified oval 202 extends outward from the standard oval 206 a relative distance S % which varies from 0 at the equatorial points to a maximum at γ°. The angle γ° is near to but not exactly 45° because of the oval shape, and the closer the aspect ratio gets to 1.0 the closer γ° is to 45°. The relative distance S % of radius $R_2$ at β° is less than that of radius $R_1$, and the relative distance S % of radius $R_3$ at α° is less than that of radius $R_2$. Although not a mirror, the same trend applies toward the vertical axis. The modified oval 202 that is calculated using the spline curves in SolidWorks therefore preferably has a maximum relative distance S % outward from a standard oval 206 of between 2-5%. Further, the aspect ratio of between 1.1-1.3 means that the maximum relative distance S % is found at an angle from the horizontal (major axis) of between 35-43°.

The potential impact of this geometry in the cross-section of the inserter tip could be a reduction of the needed cross-sectional area of the tip, thereby reducing the incision size required for delivery, and it may also reduce possible damage to the lens because of the reductions in strain and shear that are exhibited on the lens during the delivery process.

While the invention has been described in its preferred embodiments, it is to be understood that the words which have been used are words of description and not of limitation. Therefore, changes may be made within the appended claims without departing from the true scope of the invention.

What is claimed is:

1. A cartridge for receiving and delivering an intraocular lens having an optic to the inner eye, comprising:

a main body extending along a longitudinal axis from a proximal opening for receiving the intraocular lens to a distal end which defines a distal opening smaller than the intraocular lens through which the intraocular lens is expelled, the main body having a narrowing lumen extending from the proximal opening to the distal opening and defined by a luminal wall, wherein the luminal wall further has a longitudinal discontinuity or step formed in a midsection thereof and extending longitudinally for at least 0.2 cm, the longitudinal discontinuity or step configured to facilitate a spiral rolling-up or folding of the optic of the intraocular lens, wherein the longitudinal discontinuity or step is formed by the luminal wall becoming higher on a first side of a central vertical plane relative to a second side of the plane, and wherein the longitudinal discontinuity or step comprises a planar land that is angled between about 30-60° with respect to the central vertical plane, the longitudinal discontinuity or step at least partially crossing the central vertical plane.

2. The cartridge of claim 1, wherein the longitudinal discontinuity or step extends no more than 1 cm in length along the longitudinal axis.

3. The cartridge of claim 2, wherein the longitudinal discontinuity or step is centered axially at a point along the main body where a circumference of the luminal wall is approximately equal to a diameter of the optic of the intraocular lens.

4. The cartridge of claim 1, wherein the longitudinal discontinuity or step is centered axially at a point along the main body where a circumference of the luminal wall is approximately equal to a diameter of the optic of the intraocular lens.

5. The cartridge of claim 1, wherein the planar land extends a dimension A of about 0.08 inches.

6. The cartridge of claim 1, wherein the longitudinal discontinuity or step has a radial dimension of between 0.25 to 0.5 mm.

7. The cartridge of claim 1, wherein the lumen further defines a luminal shape at the distal end which deviates from a standard oval of equivalent aspect ratio such that the luminal shape is larger than the standard oval between equatorial points.

8. The cartridge of claim 1, wherein the main body has a funnel portion with a plurality of axial grooves formed in an outer surface thereof, the axial grooves being spaced apart around the outer surface.

* * * * *